US012788908B2

(12) United States Patent
Spadaro et al.

(10) Patent No.: US 12,788,908 B2
(45) Date of Patent: Nov. 10, 2026

(54) INHALATION COUNTER

(71) Applicant: PHILIP MORRIS PRODUCTS S.A., Neuchatel (CH)

(72) Inventors: Fabiana Spadaro, Lausanne (CH); Antonino Lanci, Bern (CH); Loïc Sottas, Lausanne (CH); Martin Sigrist, Bern (CH); Onur Dayioğlu, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 559 days.

(21) Appl. No.: 18/277,175

(22) PCT Filed: Feb. 22, 2022

(86) PCT No.: PCT/EP2022/054430
§ 371 (c)(1),
(2) Date: Aug. 14, 2023

(87) PCT Pub. No.: WO2022/184511
PCT Pub. Date: Sep. 9, 2022

(65) Prior Publication Data

US 2024/0115816 A1 Apr. 11, 2024

(30) Foreign Application Priority Data

Mar. 3, 2021 (EP) .................................... 21160432

(51) Int. Cl.
*A61M 15/00* (2006.01)
*A24F 42/20* (2020.01)
(Continued)

(52) U.S. Cl.
CPC ......... *A61M 15/0078* (2014.02); *A24F 42/20* (2020.01); *A24F 42/60* (2020.01);
(Continued)

(58) Field of Classification Search
CPC ............ A61M 15/003; A61M 15/0035; A61M 15/004; A61M 15/0068; A61M 15/007;
(Continued)

(56) References Cited

U.S. PATENT DOCUMENTS

2012/0240926 A1* 9/2012 Kaar ................ A61M 15/0071 235/87 R
2012/0241526 A1* 9/2012 Kaar ................ A61M 15/0078 235/87 R
2015/0374937 A1* 12/2015 Tampieri ........... A61M 15/0021 128/203.15

FOREIGN PATENT DOCUMENTS

AU 2016 204 147 7/2016
WO WO 2007/077450 7/2007
(Continued)

OTHER PUBLICATIONS

PCT International Search Report and Written Opinion for PCT/EP2022/054430 dated May 25, 2022 (8 pages).
(Continued)

*Primary Examiner* — Joseph D. Boecker
(74) *Attorney, Agent, or Firm* — Mueting Raasch Group

(57) ABSTRACT

An inhalation counter (350, 450, 550) for an inhalation system (100) is provided. The inhalation system comprises a fluid flow passage (322) and the inhalation counter comprises an escapement wheel (352, 452), a biasing means (354, 454) for incrementing the escapement wheel, a conversion mechanism which, in use, is configured to perform a first action in response to a temporary increase in fluid flow rate through the fluid flow passage, and an anchor (356, 456). The anchor is coupled to the conversion mechanism and configured to interact with the escapement wheel so as to allow the biasing means to increment the escapement wheel in response to the first action of the conversion
(Continued)

mechanism. A holder (300) and an inhalation system comprising the inhalation counter are also provided.

17 Claims, 4 Drawing Sheets

(51) Int. Cl.

| | |
|---|---|
| ***A24F 42/60*** | (2020.01) |
| ***A61M 15/06*** | (2006.01) |
| ***G06M 1/02*** | (2006.01) |
| ***G06M 1/04*** | (2006.01) |
| ***G06M 1/14*** | (2006.01) |
| ***G06M 1/16*** | (2006.01) |

(52) U.S. Cl.

CPC ...... *A61M 15/003* (2014.02); *A61M 15/0035* (2014.02); *A61M 15/004* (2014.02); *A61M 15/0071* (2014.02); *A61M 15/0075* (2014.02); *A61M 15/06* (2013.01); *G06M 1/028* (2013.01); *G06M 1/041* (2013.01); *G06M 1/14* (2013.01); *G06M 1/16* (2013.01); *A61M 15/0021* (2014.02); *A61M 2205/3334* (2013.01)

(58) Field of Classification Search

CPC .......... A61M 15/0071; A61M 15/0073; A61M 15/0075; A61M 15/0076; A61M 15/0078; A61M 15/06; A61M 2205/3334; A24F 42/20; A24F 42/60; G06M 1/028; G06M 1/041; G06M 1/14; G06M 1/143; G06M 1/16; G06M 1/163; G04B 11/006; G04B 11/008

See application file for complete search history.

(56) References Cited

FOREIGN PATENT DOCUMENTS

| | | |
|---|---|---|
| WO | WO 2021/079341 | 4/2021 |
| WO | WO 2021/079345 | 4/2021 |
| WO | WO 2021/090143 | 5/2021 |
| WO | WO 2022/018301 | 1/2022 |

OTHER PUBLICATIONS

Extended European Search Report for Application No. 21160432.7 dated Jul. 29, 2021 (8 pages).

International Preliminary Report on Patentability for PCT/EP2022/054430 dated Aug. 29, 2023 (6 pages).

* cited by examiner

INHALATION COUNTER

This application is a U.S. National Stage Application of International Application No. PCT/EP2022/054430 filed Feb. 22, 2022, which was published in English on Sep. 9, 2022, as International Publication No. WO 2022/184511 A1. International Application No. PCT/EP2022/054430 claims priority to European Application No. 21160432.7 filed Mar. 3, 2021.

The present disclosure relates to an inhalation counter for an inhalation system. The present disclosure also relates to a holder comprising the inhalation counter and to an inhalation system comprising the inhalation counter.

In some inhalation systems, it may be beneficial to be able to count a number of times a user has inhaled on the system. For example, some dry powder inhalation systems may comprise a holder and an inhaler article. The inhaler article may comprise a capsule containing a dry powder. In such dry powder inhalation systems, the inhaler article may be engaged with the holder, and the capsule may then be pierced. A user may then inhale on the holder to cause an air flow through the system. Each air flow from each inhalation may carry a portion of the dry powder from the capsule into the lungs of the user. However, after a certain number of inhalations, subsequent inhalations may not extract a significant amount, if any, of the remaining powder from the capsule. At this point, the capsule may be considered depleted. Thus, by being able to count the number of inhalations on the system, it may be possible to indicate when the user has likely finished a capsule.

Some inhalation systems address this need for an inhalation counter using electronic components. However, such electronic components may require complicated user interfaces to operate. In addition, using electronic components can increase the cost and complexity of manufacturing these systems. It is an aim of the present invention to address one or more of these issues.

According to the disclosure, there may be provided an inhalation counter. The inhalation counter may be suitable for an inhalation system. The inhalation system may comprise a fluid flow passage. The inhalation counter may comprise an escapement wheel. The inhalation counter may comprise a biasing means. The biasing means may be for incrementing the escapement wheel. The inhalation counter may comprise a conversion mechanism. In use, the conversion mechanism may be configured to perform a first action in response to a temporary increase in fluid flow rate through the fluid flow passage. The inhalation counter may comprise an anchor. The anchor may be coupled to the conversion mechanism. The anchor may be configured to interact with the escapement wheel, for example so as to allow the biasing means to increment the escapement wheel in response to the first action of the conversion mechanism.

Thus, according to a first aspect of the disclosure, there may be provided an inhalation counter suitable for an inhalation system. The inhalation system comprises a fluid flow passage. The inhalation counter comprises an escapement wheel, a biasing means for incrementing the escapement wheel, a conversion mechanism which, in use, is configured to perform a first action in response to a temporary increase in fluid flow rate through the fluid flow passage, and an anchor. The anchor is coupled to the conversion mechanism and is configured to interact with the escapement wheel so as to allow the biasing means to increment the escapement wheel in response to the first action of the conversion mechanism.

Advantageously, the inhalation counter according to the first aspect may automatically count inhalations. That is, the inhalation counter may count inhalations without any input from a user beyond inhaling on the inhalation system. This may simplify use of the inhalation counter.

Advantageously, the inhalation counter may comprise an escapement wheel. The use of an escapement wheel may ensure that the inhalation counter counts only a single inhalation regardless of whether the inhalation is deep or shallow, or whether the inhalation is long or short. Thus, the escapement wheel may allow the inhalation counter to reliably count the number of inhalations on the inhalation system regardless of the nature of the inhalation.

The inhalation counter may comprise the fluid flow passage. The inhalation counter may be coupled to, or configured to couple to, the fluid flow passage in use. The inhalation counter may be configured to couple, for example reversibly couple, to the fluid flow passage. Advantageously, this may allow the inhalation counter to be replaced or used with another inhalation system.

An inhalation on the inhalation system may result in the temporary increase in fluid flow rate through the fluid flow passage. The temporary increase in fluid flow rate may comprise a first portion in which the fluid flow rate increases. The temporary increase in fluid flow rate may comprise a second portion in which the fluid flow rate decreases. The second portion may be subsequent to the first portion.

A normal inhalation on the inhalation system may result in a fluid flow rate through the fluid flow passage increasing from zero to a maximum flow rate, and then decreasing from the maximum flow rate to zero. The fluid flow rate may increase monotonically from zero to a maximum flow rate. The fluid flow rate may decrease monotonically from the maximum flow rate to zero. Alternatively, at least one of the increase and the decrease of the fluid flow rate may be non-monotonic. As used herein, any reference to an inhalation may refer to a normal inhalation of this nature, and any reference or a fluid or air flow through the fluid flow passage may refer to a normal fluid or air flow through the fluid flow passage in response to a regular inhalation of this nature.

The conversion mechanism may be configured to initiate the first action in response to the first portion of the temporary increase in fluid flow rate. The conversion mechanism may use the energy of the fluid flow to initiate the first action. In use, the temporary increase in fluid flow rate through the fluid flow passage may cause the conversion mechanism to perform the first action. In use, the first portion of the temporary increase in fluid flow rate through the fluid flow passage may cause the conversion mechanism to initiate the first action. In use, the second portion of the temporary increase in fluid flow rate through the fluid flow passage may cause the conversion mechanism to complete the first action, for example after the first portion of the temporary increase in fluid flow rate through the fluid flow passage has caused the conversion mechanism to initiate the first action. Advantageously, this may circumvent the need for an energy source to initiate the first action.

The conversion mechanism may be configured to complete the first action in response to the second portion of the temporary increase in fluid flow rate. Advantageously, this may allow the conversion mechanism to reliably initiate and complete the first action in response to a temporary increase in fluid flow rate and therefore in response to a regular inhalation.

The inhalation counter may be, or may be referred to as, a fluid flow-activated inhalation counter.

Where the increase in fluid flow rate is not monotonic, the conversion mechanism may be configured to only complete the first action in response to the second portion of the temporary increase in fluid flow rate, and not in response to small fluctuations in the flow rate during the temporary increase in fluid flow rate. As described in more detail below, this may be achieved by providing a resistance component providing sufficient resistance to prevent the returning movement of the actuator occurring in response to very small temporary drops in fluid flow rate during the temporary increase in fluid flow rate.

The conversion mechanism may comprise an actuator. The first action may comprise movement of the actuator. In use, fluid flow, for example fluid flow through the fluid flow passage during the temporary increase in fluid flow rate, may act on a component of the conversion mechanism, for example on the actuator of the conversion mechanism or on a component coupled to the actuator of the conversion mechanism. In use, fluid flow, for example fluid flow through the fluid flow passage during the temporary increase in fluid flow rate, may act on a component of the conversion mechanism, for example on the actuator of the conversion mechanism or on a component coupled to the actuator of the conversion mechanism, to cause the conversion mechanism to perform the first action.

The first action may comprise a departing movement of the actuator from a first position to a second position. The departing movement of the actuator may occur during, or in response to, the first portion of the temporary increase in fluid flow rate. The first action may comprise a returning movement of the actuator from the second position to the first position. The returning movement of the actuator may occur during, or in response to, the second portion of the temporary increase in fluid flow rate.

The conversion mechanism may be configured to resist the departing movement of the actuator. Advantageously, this may make the inhalation counter less likely to erroneously count an inhalation in response to a very small temporary increase in fluid flow rate. In addition, the actuator may not resist the departing movement of the actuator to such an extent that the returning movement of the actuator occurs in response to a very small temporary drop in fluid flow rate.

The conversion mechanism may comprise a resistance component. The resistance component may be configured to resist the departing movement of the actuator. The resistance component may comprise one or more springs. For example, the resistance component may comprise any one or more of a helical spring, a leaf spring, a torsion spring, a spiral spring, and a disc spring.

The actuator may comprise one or more of a piston, a bellow and a membrane. Advantageously, such actuators may be straightforward to manufacture with a suitably small size and mass for use in an inhalation system.

The actuator may comprise a flap. At least a portion of the flap may be located or may be locatable in the fluid flow passage in use. In use, fluid flow through the fluid flow passage may contact the flap. This contact may exert a force on the flap in order to cause the flap to move, for example by one or more of rotation, translation, and flexing. Advantageously, this may provide a simple yet reliable conversion mechanism.

The conversion mechanism may comprise a rotatable component. The first action may comprise rotation of the rotatable component. For example, in use, the rotatable component may be configured to rotate in a first direction in response to the first portion of the temporary increase in fluid flow rate. The rotatable component may be configured to rotate in a first direction in response to a fluid flow rate in a first direction, for example, when a user inhales on an inhaler article. The conversion mechanism may prevent the rotatable component from rotating in a second direction different, for example opposite, to the first direction. Fluid may flow in a second direction opposite to the first direction if a user where to attempt to blow on the inhaler system rather than inhale. Preventing rotation of the rotatable component in a second direction may prevent the inhalation counter from being reset inadvertently. This may also advantageously prevent dry powder from the inhaler article from flowing the wrong way through the inhaler system.

For example, the conversion mechanism may comprise one or more of a ratchet and a freewheel clutch. The at least one of a ratchet and a freewheel clutch may allow the rotatable component to rotate in a first direction while preventing the rotatable component from rotating in the second direction. The rotatable component may comprise a turbine. Where the rotatable component comprises a turbine, the conversion mechanism may further comprise a means for converting the rotation movement of the turbine to a departing movement and a returning movement.

For example, the conversion mechanism may comprise one or more of a cam and follower, a crank, and a screw thread mechanism to convert the rotation movement of the turbine to a departing movement and a returning movement.

The rotatable component may be configured to rotate in a second direction different, for example opposite, to the first direction in response to the second portion of the temporary increase in fluid flow rate. The rotatable component may comprise the flap.

The conversion mechanism may comprise a flexible component and the first action may comprise flexing of the flexible component. For example, in use, the flexible component may be configured to flex in a first direction in response to the first portion of the temporary increase in fluid flow rate. And the flexible component may be configured to flex in a second direction different, for example opposite, to the first direction in response to the second portion of the temporary increase in fluid flow rate. The flexible component may comprise the flap. The flexible component may comprise the membrane. Advantageously, the use of a membrane may result in a low-friction conversion mechanism. This may allow the conversion mechanism to perform the first action even in response to small temporary increases in fluid flow rate, for example due to shallow inhalations.

The conversion mechanism may comprise a venturi tube or nozzle. The conversion mechanism may be configured to initiate the first action in response to one or both of an increase in fluid flow rate through the venturi tube or nozzle and a reduction in pressure in the venturi tube or nozzle. Advantageously, the use of a venturi tube or nozzle may result in a larger pressure differential, or fluid flow rate differential, than otherwise possible. This may allow the conversion mechanism to perform the first action even in response to small temporary increases in fluid flow rate, for example due to shallow inhalations.

The escapement wheel may comprise a plurality of teeth. The teeth of the escapement wheel may extend in a radially outward direction. Advantageously, such teeth may provide a reliable and repeatable interaction between the anchor and the escapement wheel. This may allow the biasing means to reliably increment the escapement wheel, and count a single inhalation, in response to the first action of the conversion mechanism.

The anchor may interact with the teeth of the escapement wheel in use. This may allow the biasing means to increment the escapement wheel in response to the first action of the conversion mechanism.

The anchor may comprise a first anchoring prong. The anchor may comprise a second anchoring prong. One or both of the first anchoring prong and the second anchoring prong may interact with the teeth of the escapement wheel in use. This may allow the biasing means to increment the escapement wheel in response to the first action of the conversion mechanism. The anchor may comprise a pallet fork.

In use, prior to the temporary increase in fluid flow rate, the first anchoring prong may be engaged with a first tooth of the escapement wheel. After the temporary increase in fluid flow rate, the first anchoring prong may be engaged with a second tooth of the escapement wheel. The second tooth of the escapement wheel may be adjacent to the first tooth of the escapement wheel.

In use, during the temporary increase in fluid flow rate, the second anchoring prong may engage with a third tooth of the escapement wheel.

In use, the departing movement of the actuator may disengage the first anchoring prong from the first tooth of the escapement wheel. In use, the departing movement of the actuator may engage the second anchoring prong with the third tooth of the escapement wheel, for example after disengaging the first anchoring prong from the first tooth of the escapement wheel.

In use, the returning movement of the actuator may disengage the second anchoring prong from the third tooth of the escapement wheel. In use, the returning movement of the actuator may engage the first anchoring prong with the second tooth of the escapement wheel, for example after disengaging the second anchoring prong from the third tooth of the escapement wheel.

Advantageously, these interactions between the first and second anchoring prongs of the anchor and the first, second and third teeth of the escapement wheel may provide a straightforward but reliable way to allow the biasing means to increment the escapement wheel, and count a single inhalation, in response to the first action of the conversion mechanism.

The biasing means may comprise one or more springs. For example, the biasing means may comprise any one or more of a helical spring, a leaf spring, a torsion spring, a spiral spring, and a disc spring. The biasing means may comprise a stressed material, for example a compressed material or a tensioned material. Advantageously, such biasing means may be reliable and may not need a power source.

The inhalation counter may comprise an indication means for indicating to a user information relating to an inhalation count of the inhalation counter. Advantageously, this may allow the user to determine information relating to the inhalation count of the inhalation counter.

The information relating to the inhalation count may comprise the inhalation count itself.

For example, where the information relating to the inhalation count comprises the inhalation count, the inhalation count may begin at zero. The inhalation count may, for each inhalation on the inhalation system, increase by one. The inhalation count increasing to a certain number may indicate that a consumable of the inhalation system has likely been fully consumed. For example, if a particular consumable usually requires twelve inhalations to fully consume, the inhalation count reaching twelve may indicate that the consumable is likely fully consumed.

The information relating to the inhalation count may comprise information for estimating the inhalation count.

For example, the information relating to the inhalation count may comprise information for estimating the inhalation count in the form of a progress bar. The progress bar may initially indicate zero progress. So zero progress may inform the user that zero inhalations have been performed thus far. The progress bar may, in response to one or more inhalations on the inhalation system, indicate some progress along the progress bar. So, if the indication means is configured for use with a particular consumable usually requiring twelve inhalations to fully consume and the progress bar indicates 50 percent progress, this may allow the user to estimate that six inhalations have been performed. After a predetermined number of inhalations, the progress bar may indicate 100 percent progress. So, for the above-mentioned consumable, this may allow the user to estimate that twelve or more inhalations have been performed. This may indicate that the consumable has likely been fully consumed.

The information relating to the inhalation count may comprise an estimate of a number of inhalations remaining before a consumable of the inhalation system has been fully consumed.

For example, where the information relating to the inhalation count comprises an estimate of the number of inhalations remaining before a consumable of the inhalation system has been fully consumed, the estimate may begin at a number N. The beginning number N may be adjustable, for example by a user. A user who takes deeper, longer inhalations may wish to begin with a lower beginning number N than a user who takes shallower, shorter inhalations. This is because fewer deeper and longer inhalations may be required to fully consume a consumable of the inhalation system. For each inhalation on the inhalation system, the number N may decrease by one. The number N decreasing to reach a second number M, for example zero, may indicate that the consumable has been fully consumed.

The information relating to the inhalation count may comprise information for estimating the number of inhalations remaining before a consumable of the inhalation system has been fully consumed.

For example, the information relating to the inhalation count may comprise information for estimating the number of inhalations remaining before a consumable of the inhalation system has been fully consumed in the form of a progress bar. The progress bar may initially indicate zero consumption of the consumable. Thus, the progress bar may allow a user to estimate that a certain number X of inhalations on the inhalation system may be made before the consumable has been fully consumed. For example, the user may know that a given consumable requires twelve inhalations to fully consume. So the progress bar indicating zero progress would allow the user to estimate that twelve inhalations will fully consume the consumable. The progress bar may, in response to one or more inhalations on the inhalation system, indicate consumption of the consumable along the progress bar. Thus, the progress bar may indicate information for estimating the number of inhalations remaining before a consumable of the inhalation system has been fully consumed. For example, if the progress bar indicates 50 percent progress for the above-mentioned consumable, the user can estimate that six further inhalations will fully consume the consumable. After a predetermined number of inhalations, the progress bar may indicate 100 percent progress. This may indicate that the consumable has likely been fully consumed.

Advantageously, indicating such information to a user may allow the user to easily and quickly determine useful information relating to the inhalation count.

The indication means may be coupled to one or both of the escapement wheel and the conversion mechanism. The indication means may be configured to alter the information relating to the inhalation count in response to the first action or the increment of the escapement wheel, or in response to a predetermined number of first actions or increments of the escapement wheel. Altering the information relating to the inhalation count may comprise increasing an inhalation count indicated to the user, or decreasing an estimate of the number of inhalations remaining before a consumable of the inhalation system is fully consumed.

The indication means may comprise a pointer. The indication means may comprise a scale. The indication means may comprise one or both of a linear scale and a rotary scale. The indication means may comprise a window. The indication means may comprise a display such as an electronic display. The indication means may comprise E-ink.

The pointer may be configured to move relative to the scale, for example in response to a single inhalation or in response to a predetermined number of inhalations. The pointer may be configured to move linearly relative to the scale. In this case, the scale may be termed a linear scale. The pointer may be configured to rotate relative to the scale. In this case, the scale may be termed a rotary scale. The information relating to the inhalation count may be indicated by the pointer pointing at the scale. The information relating to the inhalation count may be viewable by a user through the window.

The inhalation counter may comprise a modifying mechanism. The modifying mechanism may be coupled to the indication means. The modifying mechanism may be for resetting or otherwise modifying the information relating to the inhalation count.

The modifying mechanism may be configured to allow the user to set the information relating to the inhalation count. For example, as explained above, the user may be able to set a beginning number N which decreases with each inhalation on the inhalation system.

The modifying mechanism may comprise a freewheel clutch. The freewheel clutch may be coupled to one or both of the escapement wheel and the biasing means. The freewheel clutch may be configured to rotate in a first direction to modify the information relating to the inhalation count. The freewheel clutch may be configured to rotate in a second direction, opposite to the first direction, without modifying the information relating to the inhalation count.

As explained in more detail below, the inhalation counter may form part of an inhalation system comprising a holder and an inhaler article. For example, the holder may comprise the inhalation counter. The modifying mechanism may be configured to reset or otherwise modify the information relating to the inhalation count upon one or both of engaging an inhaler article with the holder and disengaging the inhaler article from the holder. The modifying mechanism comprising a freewheel clutch may be particularly advantageous in this case as the freewheel clutch may provide a straightforward mechanism for one of engaging the inhaler article with the holder and disengaging the inhaler article from the holder to modify the information, but the other of engaging the inhaler article with the holder and disengaging the inhaler article from the holder to not modify the information. For example, one of engaging the inhaler article with the holder and disengaging the inhaler article from the holder may cause the freewheel clutch to rotate in the first direction. And the other of engaging the inhaler article with the holder and disengaging the inhaler article from the holder may cause the freewheel clutch to rotate in the second direction. In some examples, one or both of engaging the inhaler article with the holder and disengaging the inhaler article from the holder may reset the information relating the inhalation count, for example reset an inhalation count to zero, or reset the count to a beginning number N which decreases with each inhalation on the inhalation system. Advantageously, this may circumvent the need for a separate user action to modify the information relating to the inhalation count.

The inhalation counter may comprise an energising mechanism for energising the biasing means. Advantageously, this may remove the need for a power source to energise the biasing means.

The energising mechanism may be configured to allow the user to energise the biasing means. The energising mechanism may comprise a freewheel clutch. The freewheel clutch may be coupled to one or both of the escapement wheel and the biasing means. The freewheel clutch may be configured to rotate in a first direction to energise the biasing means. The freewheel clutch may be configured to rotate in a second direction, opposite to the first direction, without energising the biasing means and without de-energising the biasing means.

As explained in more detail below, the inhalation counter may form part of an inhalation system comprising a holder and an inhaler article. For example, the holder may comprise the inhalation counter. The energising mechanism may be configured to energise the biasing means upon one or both of engaging an inhaler article with the holder and disengaging the inhaler article from the holder. The energising mechanism comprising a freewheel clutch may be particularly advantageous in this case as the freewheel clutch may provide a straightforward mechanism for one of engaging the inhaler article with the holder and disengaging the inhaler article from the holder to energise the biasing means, but the other of engaging the inhaler article with the holder and disengaging the inhaler article from the holder to neither energise nor de-energise the biasing means. For example, one of engaging the inhaler article with the holder and disengaging the inhaler article from the holder may cause the freewheel clutch to rotate in the first direction. And the other of engaging the inhaler article with the holder and disengaging the inhaler article from the holder may cause the freewheel clutch to rotate in the second direction. Advantageously, this may circumvent the need for a separate user action to energise the biasing means.

The inhalation counter may comprise a combined modifying and energising mechanism. This mechanism may be suitable for modifying the information relating to the inhalation count and energising the biasing means. The combined modifying and energising mechanism may be configured to allow the user to modify the information relating to the inhalation count and energise the biasing means. Advantageously, this may mitigate a need for a power source to energise the biasing means.

The combined modifying and energising mechanism may be configured to modify the information relating to the inhalation count and energise the biasing means simultaneously.

The combined modifying and energising mechanism may comprise a freewheel clutch. The freewheel clutch may be coupled to the escapement wheel and the biasing means. The freewheel clutch may be configured to rotate in a first direction to modify the information relating to the inhalation count and energise the biasing means. The freewheel clutch may be configured to rotate in a second direction, opposite to the first direction, without modifying the information relating to the inhalation count or energising the biasing means.

As explained in more detail below, the inhalation counter may form part of an inhalation system comprising a holder and an inhaler article. For example, the holder may comprise the inhalation counter. The combined modifying and energising mechanism may be configured to modify the information relating to an inhalation count and energise the biasing means upon one or both of engaging an inhaler article with the holder and disengaging the inhaler article from the holder. The combined modifying and energising mechanism comprising a freewheel clutch may be particularly advantageous in this case as the freewheel clutch may provide a straightforward mechanism for one of engaging the inhaler article with the holder and disengaging the inhaler article from the holder to modify the information relating to an inhalation count and energise the biasing means, but the other of engaging the inhaler article with the holder and disengaging the inhaler article from the holder to not modify the information relating to an inhalation count and neither energise nor de-energise the biasing means. For example, one of engaging the inhaler article with the holder and disengaging the inhaler article from the holder may cause the freewheel clutch to rotate in the first direction. And the other of engaging the inhaler article with the holder and disengaging the inhaler article from the holder may cause the freewheel clutch to rotate in the second direction. Advantageously, this may circumvent the need for a separate user action to modify the information relating to an inhalation count and energise the biasing means.

As used herein, and in particular with reference to the modifying mechanism, the energising mechanism, and the combined modifying and energising mechanism, engaging the inhaler article with the holder may comprise one or both of receiving at least a portion of the inhaler article in the holder, and motion of the inhaler article relative to the holder. The motion of the inhaler article relative to the holder may occur when at least a portion of the inhaler article is received in the holder. The motion of the inhaler article relative to the holder may comprise motion to activate or pierce or rupture a capsule of the inhaler article.

As used herein, and in particular with reference to the modifying mechanism, the energising mechanism, and the combined modifying and energising mechanism, disengaging the inhaler article from the holder may comprise one or both of withdrawal of at least a portion of the inhaler article from the holder, and motion of the inhaler article relative to the holder. The motion of the inhaler article relative to the holder may occur when at least a portion of the inhaler article is received in the holder. The motion of the inhaler article relative to the holder may comprise motion of the inhaler article following activation, piercing, or rupturing a capsule of the inhaler article.

So, as an example to illustrate the use of a combined modifying and energising mechanism, the combined modifying and energising mechanism may allow a user to reset the information relating to the inhalation count and energise the biasing means in a single motion, for example by inserting an inhaler article into a cavity of the holder. More specifically, inserting an inhaler article into the cavity may reset the inhalation count to zero and energise the biasing means by compressing a spring of the biasing means.

The inhalation counter may be a mechanical inhalation counter. The inhalation counter may consist of non-electrical components. The inhalation counter may function absent an electrical power source. Advantageously, this may make the inhalation counter cheaper to manufacture.

According to the disclosure, there is provided a holder. The holder may be suitable for use with an inhaler article. The holder and inhaler article may together be considered an inhalation system. The holder may comprise an inhalation counter. The inhalation counter may comprise any one or more features described in relation to the inhalation counter according to the first aspect. The inhalation counter may comprise or be the inhalation counter according to the first aspect.

According to a second aspect of the disclosure, there is provided a holder for use with an inhaler article. The holder comprises an inhalation counter according to the first aspect.

The holder and inhaler article may together be considered an inhalation system.

The holder may comprise a fluid flow inlet. The holder may comprise a fluid flow outlet. A fluid flow passage, such as the fluid flow passage referred to in relation to the first aspect, may extend between the fluid flow inlet and the fluid flow outlet. The holder may comprise a mouthpiece.

The holder may be configured to engage with the inhaler article. The holder may be configured to receive at least a portion of the inhaler article. The holder may comprise a cavity for receiving at least a portion of the inhaler article. The holder may comprise a housing. The housing may define the cavity. The housing may define one or both of the fluid flow inlet and the fluid flow outlet.

In use, a user may inhale on an inhaler article engaged with the holder, or on a mouthpiece of the holder. This may result in a fluid flow, specifically an air flow, in through the fluid flow inlet, then through the fluid flow passage, then out through the fluid flow outlet. The fluid flow may then flow through or past the inhaler article. Fluid flowing through or past the inhaler article may entrain an aerosol component from the inhaler article. This may form an aerosol. The aerosol component may comprise one or more of a solid aerosol component such as a dry powder, a liquid aerosol component such as a suspended droplet of a liquid, and a gaseous aerosol component such as a vaporised liquid aerosol component. The fluid flow may entrain a solid aerosol component or a liquid aerosol component to form an aerosol. The fluid flow may entrain a gaseous aerosol component which subsequently cools and condenses to form an aerosol. The aerosol may then flow into the mouth of the user, for example through the inhaler article or the mouthpiece.

The holder may comprise a piercing or rupturing means. The piercing or rupturing means may comprise a piercing element such as a spike. The piercing or rupturing means may be configured to pierce or rupture the capsule of the inhaler article. The piercing or rupturing means may be configured to extend into the cavity to pierce or rupture the capsule of the inhaler article. The holder may comprise a sleeve. The sleeve may be moveable relative to the piercing or rupturing means. The sleeve may define the cavity. In use, an inhaler article may be partially received in the cavity defined by the sleeve. The sleeve and inhaler article may be configured to move together relative to a housing of the holder. The sleeve and inhaler article may be configured to move together relative to the piercing or rupturing means, for example until the piercing or rupturing means pierces or ruptures a capsule of the inhaler article.

Movement of the sleeve relative to a housing of the holder may be used to operate one or both of the modifying mechanism and the energising mechanism. Operation of the modifying mechanism may refer to modifying the information relating to the inhalation count and operation of the energising mechanism may refer to energising the biasing means. Movement of the sleeve relative to a housing of the holder may be used to operate the combined modifying and energising mechanism. Operation of the combined modifying and energising mechanism may refer to modifying the information relating to the inhalation count and energising the biasing means.

The inhaler article may comprise or may be a consumable, for example the consumable referred to in relation to the first aspect. The inhaler article may comprise a capsule, for example a capsule containing a dry powder. The holder may comprise or may be a dry powder inhaler.

In use, a user may engage the holder with an inhaler article comprising a capsule containing a dry powder. The user may then operate the device so as to pierce the capsule with a piercing element of the holder. The user may then inhale on the inhaler article, or on a mouthpiece of the holder. Such an inhalation may result in air flowing in through the fluid flow inlet of the holder. This air may then flow through the fluid flow passage. The inhalation may cause a temporary increase in fluid flow rate through the fluid flow passage, as referred to in relation to the first aspect. This temporary increase in fluid flow rate may alter the information relating to the inhalation count indicated to the user by an indication means of an inhalation counter of the holder. The fluid flow through the fluid flow passage may entrain the dry powder from the capsule. The fluid and dry powder may form an aerosol in the fluid flow path. The aerosol may then be delivered to the user. After the consumable has been fully consumed, the inhaler article may be disengaged from the holder. The holder may be then be usable with another, fresh inhaler article.

The holder may comprise an inhalation volume estimator. The inhalation volume estimator may comprise an indicator for indicating inhalation volume information relating to a volume of fluid flow through the fluid flow passage.

Advantageously, the combination of an inhalation counter and an inhalation volume estimator may give a user more information about their inhalations. This may allow the user to more accurately determine when a consumable has been fully consumed.

As explained above, the inhalation counter may comprise one or more of a modifying mechanism, an energising mechanism, and a combined modifying and energising mechanism. And any one, two, or all of these mechanisms may be operated by one or both of engaging the inhaler article with the holder and disengaging the inhaler article from the holder. Further details are explained above with reference to the inhalation counter. Advantageously, this may circumvent the need for a separate user action to modify the information relating to an inhalation count or energise the biasing means.

The holder may be a mechanical holder. The holder may consist of non-electrical components. The holder may function absent an electrical power source. Advantageously, this may make the inhalation counter cheaper to manufacture.

The holder may comprise the inhalation counter comprising the indication means described above. Alternatively, or in addition, the holder may comprise an indication means having any one or more of the features of the indication means of the inhalation counter described above.

According to the disclosure, there may be provided an inhalation system. The system may comprise a holder according to the second aspect. The system may comprise the inhaler article referred to in relation to the second aspect.

According to a third aspect of the disclosure, there is provided an inhalation system. The system comprises a holder according to the second aspect. The system further comprises the inhaler article referred to in relation to the second aspect.

The inhalation system may be a dry powder inhalation system. The holder may be a dry powder inhaler. The inhaler article may comprise a dry powder, for example contained in a capsule of the inhaler article.

The capsule may contain one or both of nicotine particles and flavour particles. The flavour particles may be larger than the nicotine particles. In use, the flavour particles may assist in transporting the nicotine particles into the lungs of the user. The flavour particles may preferentially remain in the mouth or buccal cavity of the user. In use, one or both of nicotine particles and the flavour particles may be delivered at flow rates that are within conventional smoking regime flow rates.

As used herein, the term "fluid flow" may refer to air flow. The fluid flow passage may be an air flow passage. An inhalation on the inhalation system may result in the temporary increase in fluid flow through the fluid flow passage.

As used herein, the term "nicotine" may refer to nicotine and nicotine derivatives such as free-base nicotine, nicotine salts and the like.

As used herein, the term "flavour" may refer to organoleptic compounds, compositions, or materials that alter and are intended to alter the taste or aroma characteristics of nicotine during consumption or inhalation thereof.

The invention is defined in the claims. However, below there is provided a non-exhaustive list of non-limiting examples. Any one or more of the features of these examples may be combined with any one or more features of another example, embodiment, or aspect described herein.

1. An inhalation counter for an inhalation system, the inhalation system comprising a fluid flow passage and the inhalation counter comprising:
   - an escapement wheel;
   - a biasing means for incrementing the escapement wheel;
   - a conversion mechanism which, in use, is configured to perform a first action in response to a temporary increase in fluid flow rate through the fluid flow passage; and
   - an anchor,
   - wherein the anchor is coupled to the conversion mechanism and configured to interact with the escapement wheel so as to allow the biasing means to increment the escapement wheel in response to the first action of the conversion mechanism.
2. An inhalation counter according to example 1, wherein the inhalation counter comprises the fluid flow passage or is configured to couple to the fluid flow passage in use.
3. An inhalation counter according to example 1 or 2, wherein the temporary increase in fluid flow rate comprises a first portion in which the fluid flow rate increases, and a subsequent second portion in which the fluid flow rate decreases, and the conversion mechanism is configured to initiate the first action in response to the first portion of the temporary increase in fluid flow rate.
4. An inhalation counter according to example 3, wherein the conversion mechanism is configured to complete the first action in response to the second portion of the temporary increase in fluid flow rate.

5. An inhalation counter according to any preceding example, wherein the conversion mechanism comprises an actuator and the first action comprises movement of the actuator.
6. An inhalation counter according to example 5, wherein the first action comprises a departing movement of the actuator from a first position to a second position, and a returning movement of the actuator from the second position to the first position.
7. An inhalation counter according to example 6, wherein the conversion mechanism is configured to resist the departing movement of the actuator.
8. An inhalation counter according to example 7, wherein the conversion mechanism comprises a resistance component, and the resistance component is configured to resist the departing movement of the actuator.
9. An inhalation counter according to example 7 or 8, wherein the resistance component comprises a spring.
10. An inhalation counter according to any of examples 5 to 9, wherein the actuator comprises one or more of a piston, a bellow and a membrane.
11. An inhalation counter according to any of examples 5 to 10, wherein the actuator comprises a flap, and optionally wherein at least a portion of the flap is located or is locatable in the fluid flow passage in use.
12. An inhalation counter according to any preceding example, wherein the conversion mechanism comprises a rotatable component and the first action comprises rotation of the rotatable component.
13. An inhalation counter according to example 12, wherein the rotatable component comprises a turbine.
14. An inhalation counter according to any preceding example, wherein the conversion mechanism comprises a flexible component and the first action comprises flexing of the flexible component.
15. An inhalation counter according to any preceding example, wherein the conversion mechanism comprises a venturi tube or nozzle, and the conversion mechanism is configured to initiate the first action in response to one or both of an increase in fluid flow rate through the venturi tube or nozzle and a reduction in pressure in the venturi tube or nozzle.
16. An inhalation counter according to any preceding example, wherein the escapement wheel comprises a plurality of teeth.
17. An inhalation counter according to example 16, wherein the anchor interacts with the teeth of the escapement wheel in use to allow the biasing means to increment the escapement wheel in response to the first action of the conversion mechanism.
18. An inhalation counter according to any preceding example, wherein the anchor comprises a first anchoring prong and a second anchoring prong, and wherein the first anchoring prong and the second anchoring prong interact with the teeth of the escapement wheel in use to allow the biasing means to increment the escapement wheel in response to the first action of the conversion mechanism.
19. An inhalation counter according to any preceding example, wherein the biasing means comprises a spring.
20. An inhalation counter according to example 19, wherein the biasing means comprises a spiral spring.
21. An inhalation counter according to example 19 or 20, wherein the biasing means comprises a helical spring.
22. An inhalation counter according to any preceding example, wherein the inhalation counter comprises an indication means for indicating to a user information relating to an inhalation count of the inhalation counter.
23. An inhalation counter according to example 22, wherein the indication means is coupled to one or both of the escapement wheel and the conversion mechanism.
24. An inhalation counter according to example 22 or 23, wherein the indication means is configured to alter the information relating to the inhalation count in response to the first action or the increment of the escapement wheel, or in response to a predetermined number of first actions or increments of the escapement wheel.
25. An inhalation counter according to any of examples 22 to 24, wherein the indication means comprises one or both of a pointer and a scale.
26. An inhalation counter according to example 25, wherein the inhalation counter comprises the pointer and the scale and, in use, the pointer is configured to move relative to the scale in response to a single inhalation or in response to a predetermined number of inhalations.
27. An inhalation counter according to any of examples 22 to 26, wherein the inhalation counter comprises a modifying mechanism coupled to the indication means for resetting or otherwise modifying the information relating to the inhalation count.
28. An inhalation counter according to example 27, wherein the modifying mechanism is configured to allow the user to set the information relating to the inhalation count.
29. An inhalation counter according to any of examples 27 to 28, wherein the modifying mechanism comprises a freewheel clutch.
30. An inhalation counter according to any preceding example, comprising an energising mechanism for energising the biasing means.
31. An inhalation counter according to example 30, wherein the energising mechanism comprises a freewheel clutch.
32. An inhalation counter according to any of examples 22 to 26, comprising a combined modifying and energising mechanism for modifying the information relating to the inhalation count and energising the biasing means.
33. An inhalation counter according to example 32, wherein the combined modifying and energising mechanism comprises a freewheel clutch.
34. An inhalation counter according to example 33, wherein the freewheel clutch is coupled to the escapement wheel and the biasing means.
35. An inhalation counter according to example 34, wherein the freewheel clutch is configured to rotate in a first direction to modify the information relating to the inhalation count and energise the biasing means.
36. An inhalation counter according to example 35, wherein the freewheel clutch is configured to rotate in a second direction, opposite to the first direction, without modifying the information relating to the inhalation count or energising the biasing means.
37. An inhalation counter according to any of examples 32 to 36, wherein the combined modifying and energising mechanism is configured to modify the information relating to the inhalation count and energise the biasing means simultaneously.

38. An inhalation counter according to any preceding example, wherein the inhalation counter is a mechanical inhalation counter consisting of non-electrical components.
39. A holder for use with an inhaler article, the holder comprising an inhalation counter according to any preceding example.
40. A holder according to example 39, wherein the inhalation counter is an inhalation counter according to any of examples 27 to 29, and wherein the modifying mechanism is operated by one or both of engaging the inhaler article with the holder and disengaging the inhaler article from the holder.
41. A holder according to example 39 or 40, wherein the inhalation counter is an inhalation counter according to any of examples 30 to 31, and wherein the energising mechanism is operated by one or both of engaging the inhaler article with the holder and disengaging the inhaler article from the holder.
42. A holder according to example 39, wherein the inhalation counter is an inhalation counter according to any of examples 32 to 37, and wherein the combined modifying and energising mechanism is operated by one or both of engaging the inhaler article with the holder and disengaging the inhaler article from the holder.
43. A holder according to any of examples 39 to 42, wherein the holder is a mechanical holder consisting of non-electrical components.
44. A holder according to any of examples 39 to 43, wherein the holder comprises an indication means for indicating to a user information relating to an inhalation count of the inhalation counter.
45. An inhalation system comprising a holder according to any of examples 39 to 44 and the inhaler article.
46. An inhalation system according to example 45, wherein the system is a dry powder inhalation system.

Examples will now be further described with reference to the figures in which.

Figure 1:
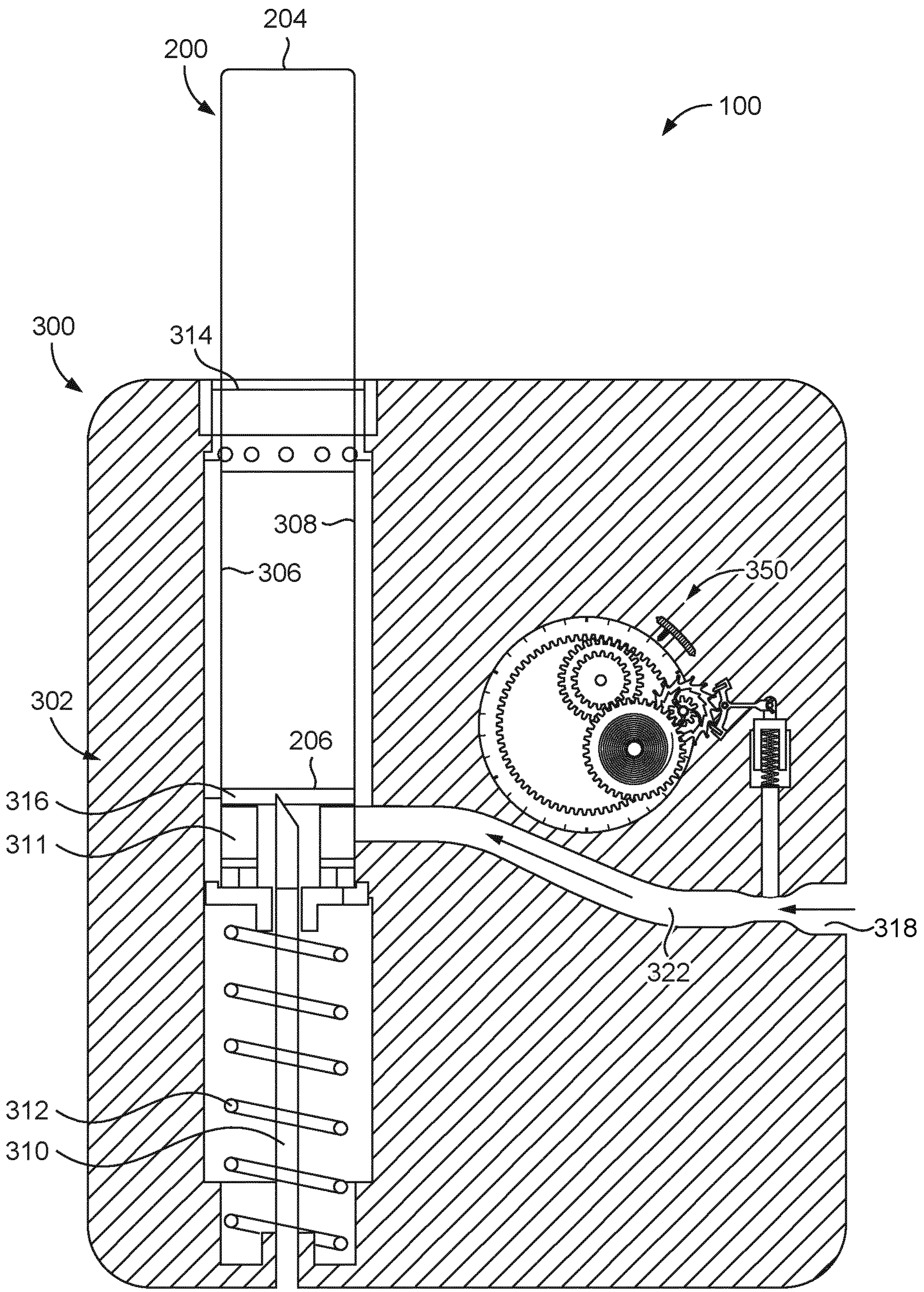
FIG. 1 is a cross-sectional view of an inhalation system comprising a holder and an inhaler article.

FIG. 1 is a cross-sectional view of an inhalation system 100. The inhalation system 100 is a mechanical inhalation system consisting of non-electrical components. The inhalation system 100 comprises an inhaler article 200 and a holder 300 receiving the inhaler article 200.

The inhaler article 200 includes a body extending along an inhaler longitudinal axis from a mouth end 204 to a distal end 206. The mouth end 204 is for insertion into a mouth of a user. The distal end 206 opposes the mouth end 204. The inhaler article 200 comprises a capsule cavity disposed within the body and bounded downstream by a filter element and bounded upstream by an open tubular element defining a central passage. As used herein, the terms "upstream" and "downstream" refer to relative positions of components relative to a direction of fluid flow through the system during normal use. The inhaler article 200 comprises a capsule disposed within the capsule cavity. The central passage of the open tubular element forms an air inlet aperture extending from the distal end 206 of the body to the capsule cavity. The central passage has a smaller diameter than the capsule. As such, the capsule cannot fall through the central passage. The capsule comprises a dry powder. The dry powder comprises nicotine particles and flavour particles.

The holder 300 comprises a housing 302 defining a housing cavity. The holder 300 comprises a movable sleeve 306. The housing cavity is for receiving and retaining the sleeve 306. The sleeve 306 defines a sleeve cavity 308. The sleeve cavity 308 is for receiving and retaining the inhaler article 200. In FIG. 1, the inhaler article 200 is shown received in the sleeve cavity 308, and the sleeve 306 is shown received in the housing cavity.

The holder 300 comprises a piercing element 310 fixed to a distal end of the housing 302 and extending along a longitudinal axis of the holder 300 towards the housing cavity. The piercing element 310 is configured to activate or pierce the capsule disposed within the inhaler article 200. The holder 300 comprises a spring 312 configured to bias the sleeve 306 away from the piercing element 310. The holder comprises a sleeve resting component 311. In a resting position of the holder 300, as shown in FIG. 1, the sleeve 306 rests on the sleeve resting component 311 and the sleeve resting component 311 rests on the spring 312. The sleeve resting component 311 comprises a central opening. In use, the piercing element 310 is able to extend through the central opening of the sleeve resting component 311 when the sleeve 306 and sleeve resting component 311 are moved towards the piercing element 310 against the action of the spring 312.

The sleeve 306 comprises a first open end 314 and a second opposing end 316. The second opposing end 316 of the sleeve 306 comprises a central opening. This central opening is configured to allow an air flow to enter the sleeve cavity 308. This central opening is configured to allow the piercing element 310 to enter the sleeve cavity 308 when the sleeve 306 is moved along the longitudinal axis of the holder 300 towards the piercing element 310.

The holder 300 comprises a fluid flow inlet 318 and a fluid flow passage 322 extending from the fluid flow inlet 318 to the second end 316 of the sleeve 306. The holder 300 comprises an inhalation counter 350 coupled to the fluid flow passage 322.

In use, a user inserts the inhaler article 200 into the sleeve cavity 308 of the holder 300. The inhalation system 100 appears as shown in FIG. 1 at this stage. The user then presses the inhaler article 200 in the direction of the distal end 206 of the inhaler article 200. This compresses the spring 312 and moves the inhaler article 200, the sleeve 306, and the sleeve resting component 311 in a distal direction relative to the housing 302. As this happens, the piercing element 310 extends through the central opening of the sleeve resting component 311, then through the central opening of the sleeve 306, then into the sleeve cavity 308, then into the capsule cavity, before contacting and piercing the capsule. The user may then release the inhaler article 200. This will allow the spring 312 to expand and move the inhaler article 200, the sleeve 306, and the sleeve resting component 311 in a proximal direction relative to the housing 302, back to the resting position shown in FIG. 1. However, at this stage, the capsule has been pierced.

A user may then inhale on the mouth end 204 of the inhaler article 200. This causes air to flow in through the fluid flow inlet 318 of the holder 300 and through the fluid flow passage 322. This air flows through the central opening of the sleeve 306, then through the central opening of the inhaler article 200 and into the capsule cavity. Dry powder from the capsule is entrained by this air flow to form an aerosol. This aerosol flows through the filter element and is delivered to the user. The air flow path is indicated with several arrows in FIG. 1. The user may repeatedly inhale on the inhaler article 200. Each inhalation results in a temporary increase in fluid flow rate through the fluid flow passage 322. Each inhalation is counted by the inhalation counter 350 and an indication means of the holder 300 indicates to the user information relating to the inhalation count of the inhalation counter 350 through a viewing window of the holder 300. The interaction between the fluid flow and the inhalation counter 350 is explained in more detail below with reference to FIG. 2. After the capsule is fully consumed, for example after twelve inhalations, the indication means indicates this to the user. The user may then withdraw the inhaler article 200 from the holder 300. This action resets the inhalation counter 350 and energises a biasing means of the inhalation counter. This is described in more detail below.

Figure 2:
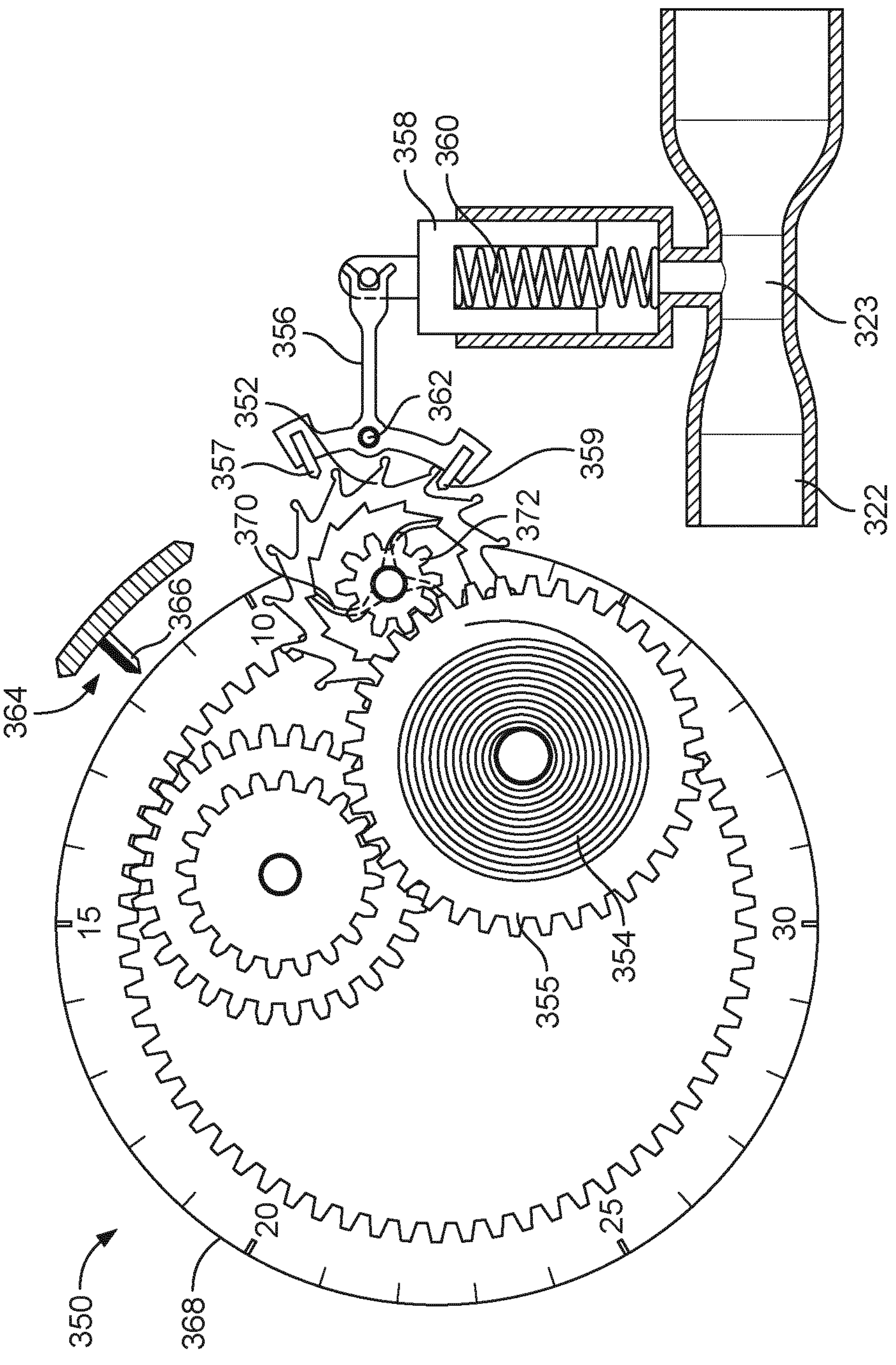
FIG. 2 is a cross-sectional view of an inhalation counter of the inhalation system of FIG. 1.

FIG. 2 shows the inhalation counter 350 of the holder 300. The inhalation counter 350 is coupled to the fluid flow passage 322 via a venturi tube 323. The inhalation counter 350 comprises an escapement wheel 352, a biasing means 354 in the form of a spiral spring for incrementing the escapement wheel 352, and a conversion mechanism. The conversion mechanism is configured to perform a first action in response to a temporary increase in fluid flow rate through the fluid flow passage 322. The inhalation counter 350 also comprises an anchor 356. The anchor 356 is coupled to the conversion mechanism and configured to interact with the escapement wheel 352 so as to allow the biasing means 354 to increment the escapement wheel 352 in response to the first action of the conversion mechanism. Specifically, the anchor 356 comprises a first anchoring prong 357 and a second anchoring prong 359, and the first anchoring prong 357 and the second anchoring prong 359 interact with teeth of the escapement wheel 352 to allow the biasing means 354 to increment the escapement wheel 352 in response to the first action of the conversion mechanism.

The conversion mechanism comprises an actuator 358 in the form of a piston. The conversion comprises a resistance component 360 in the form of a helical spring. The resistance component 360 is coupled to the actuator 358.

In use, an inhalation on the inhaler article 200 results in a temporary increase in fluid flow rate through the fluid flow passage 322, as explained above. The temporary increase in fluid flow rate may comprise a first portion in which the fluid flow rate increases, and a subsequent second portion in which the fluid flow rate decreases.

As the user inhales on the inhaler article 200, a fluid flow, specifically an air flow, is drawn in through the fluid flow inlet 318 of the holder 300. This fluid flow accelerates as it passes through the venturi tube 323 and results in a reduction in pressure in the venturi tube 323. This reduction in pressure acts to initiate the first action of the conversion mechanism.

The first action comprises movement of the actuator 358. Specifically, the first action comprises a departing movement of the actuator 358 from a first position to a second position, and a returning movement of the actuator 358 from the second position to the first position. The resistance component 360 is configured to resist the departing movement of the actuator 358.

In the inhalation counter 350 of FIG. 2, the departing movement of the actuator 358 comprises downward movement of the actuator 358. Thus, as a user begins to inhale on the inhaler article, the actuator 358 moves downwards, compressing the resistance component 360. This moves the anchor 356. Specifically, due to the coupling between the actuator 358 and the anchor 356, downward motion of the anchor 356 results in the anchor 356 pivoting clockwise about a pivot point 362 of the anchor 356. This disengages the first anchoring prong 357 of the anchor 356 from a first tooth of the escapement wheel 352. This allows the escapement wheel 352 to rotate a small amount under the action of the biasing means 354 before the second anchoring prong 359 of the anchor 356 engages a second tooth of the escapement wheel 352 to prevent further rotation. Thus, the first portion of the temporary increase in fluid flow results in less than a single increment of the escapement wheel 352. Whilst the fluid flow rate through the fluid flow passage 322 is sufficiently high, the pressure in the venturi tube 323 will be sufficiently low so as to retain the actuator 358 in its second position, thereby preventing further rotation of the escapement wheel 352 under the action of the biasing means 354.

Eventually, the fluid flow rate through the fluid flow passage 322 will begin to decrease. This is the second portion of the temporary increase in fluid flow rate. During, or very shortly after, this second portion of the temporary increase in fluid flow rate, the flow rate through the venturi tube 323 will decrease and the pressure in the venturi tube 323 will increase towards atmospheric pressure. As the pressure increases, the resistance component 360 expands and the actuator 358 moves upwards. That is, in a returning movement of the actuator 358, the actuator 358 returns from its second position back to its first position. As this happens, the anchor 356 rotates anti-clockwise about its pivot point 362. This disengages the second anchoring prong 359 from the second tooth of the escapement wheel 352. The escapement wheel 352 is then allowed to rotate a small amount under the action of the biasing means 354 before the first anchoring prong 357 engages with a third tooth of the escapement wheel 352. In this embodiment, the third tooth of the escapement wheel 352 is located adjacent to, and immediately behind, the first tooth of the escapement wheel 352. Thus, following the first action of the conversion mechanism, the escapement wheel 352 has undergone a single increment under the action of the biasing means 354.

The inhalation counter 350 further comprises an indication means 364 for indicating to a user information relating to an inhalation count of the inhalation counter 350. The indication means 364 comprises a pointer 366 and a substantially circular scale 368. The scale 368 is numbered from 0 to 29 along its outer surface. The pointer 366 remains fixed relative to the housing 302 of the holder 300 and points towards one of the numbers on the scale 368. Through the viewing window on the holder 300, a user can see the number towards which the pointer 366 is pointing at any given time. The scale 368 of the indication means 364 is coupled to the escapement wheel 352 so as to rotate relative to the pointer 366 when the escapement wheel 352 rotates. Thus, an incremental rotation of the escapement wheel 352 leads to a corresponding incremental rotation of the scale 368 relative to the pointer 366. In this sense, the scale 368 may be termed a rotary scale. In response to an inhalation, the first action of the actuator 358 causes the escapement wheel 352 and the scale 368 to be incremented, thus causing the pointer 366 to point at the subsequent number on the scale 368. In the embodiment shown in FIG. 1, each inhalation results in the number pointed at by the pointer 366 increasing by one. Thus, if the number is set to zero before the first inhalation, the inhalation counter 350 counts the number of inhalations on the inhaler article 200 and indicates this inhalation count to the user. However, as will be clear to one skilled in the art, the indication means 364 could indicate information to the user relating to the inhalation count in a number of ways. For example, the inhalation counter 350 could count down rather than count up. Equally, the gearing ratio between the scale 368 and the escapement wheel 352 could be adjusted such that the scale 368 rotates by a significantly smaller angle than the escapement wheel 352, and the scale 368 could simply include a coloured surface which, in response to inhalations, slowly fills the viewing window. Filling the viewing window could indicate that the inhaler article 200 has likely been fully consumed.

The inhalation counter 350 also comprises a combined modifying and energising mechanism (not shown). The combined modifying and energising mechanism is a manual winding mechanism on the holder 300 coupled to the scale 368. The user is able to manually rotate the winding mechanism to reduce, for example reset to zero, the inhalation count shown by the indication means 364. Due to the gearing mechanism shown in FIG. 2, as the user rotates the winding mechanism to reduce the inhalation count, the biasing means 354 is re-energised. This is because, the biasing means 354, in the form of a spiral spring, is coupled to a biasing means gear 355 which rotates as the winding mechanism is rotated, and this rotation causes energising (in other words, tightening or re-winding) of the biasing means 354.

The escapement wheel 352 does not rotate as the winding mechanism is rotated in this direction. This is because the escapement wheel 352 is coupled to an escapement wheel gear 372 by a freewheel clutch 370. Thus, when this gear rotates in an anti-clockwise direction, the scale 368 and the escapement wheel 352 rotate in a clockwise direction. But when this gear rotates in a clockwise direction, the scale 368 rotates in an anti-clockwise direction and the escapement wheel 352 does not rotate.

As would be clear to one skilled in the art, one could include a suitable mechanism such that the combined modifying and energising mechanism is operated by inserting the inhaler article 200 into the sleeve cavity, or removing the inhaler article 200 from the sleeve cavity.

Figure 3:
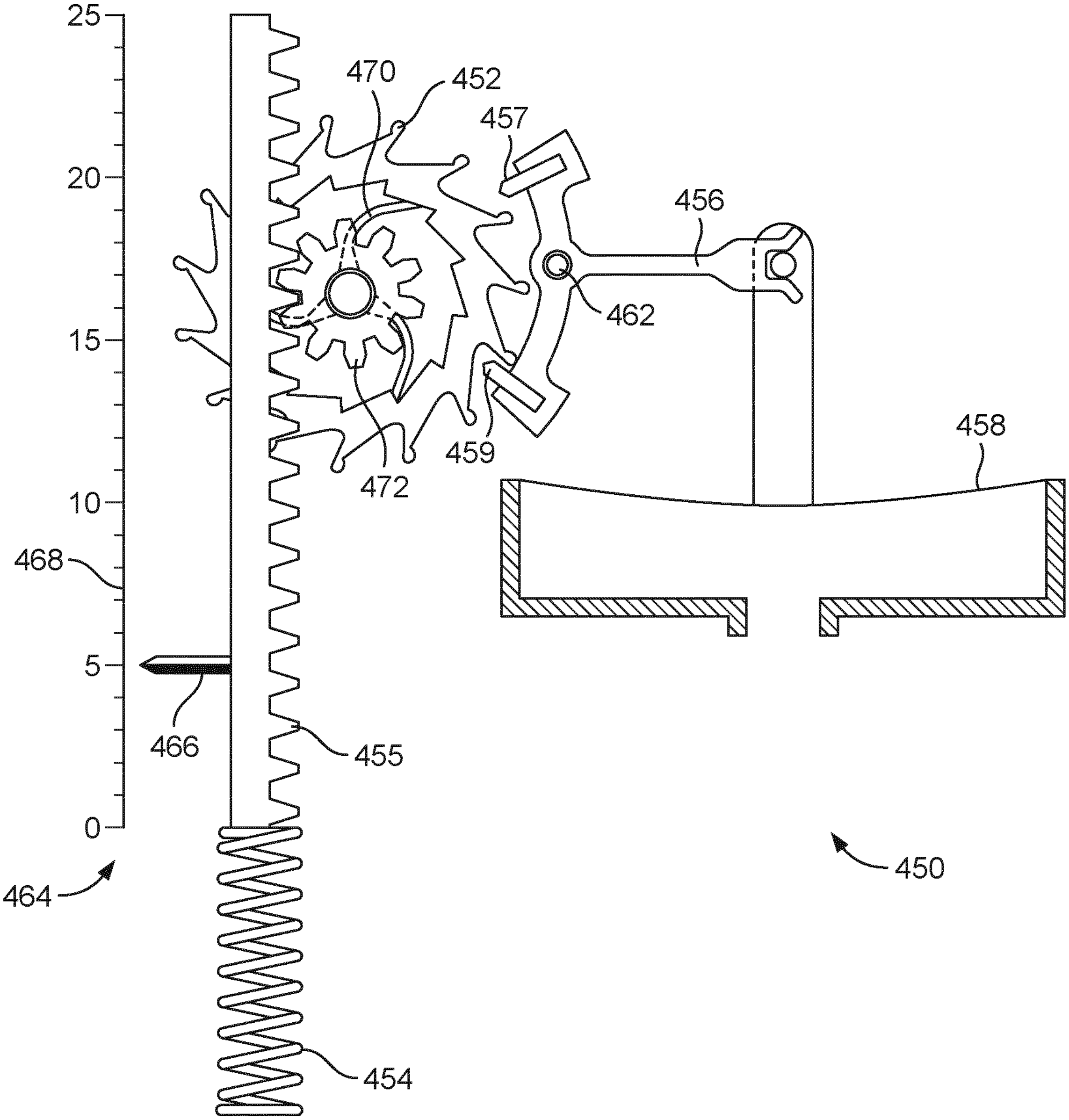
FIG. 3 is a cross-sectional view of a first alternative inhalation counter for an inhalation system.

FIG. 3 is a cross-sectional view of a first alternative inhalation counter 450 for an inhalation system. For example, the inhalation counter 450 could replace the inhalation counter 350 used in the inhalation system of FIG. 1.

The inhalation counter 450 would be coupled to the fluid flow passage 322 via a venturi tube (not shown). The inhalation counter 450 comprises an escapement wheel 452, a biasing means 454 in the form of a helical spring for incrementing the escapement wheel 452, and a conversion mechanism. The conversion mechanism is configured to perform a first action in response to a temporary increase in fluid flow rate through the fluid flow passage 322. The inhalation counter 450 also comprises an anchor 456. The anchor 456 is coupled to the conversion mechanism and configured to interact with the escapement wheel 452 so as to allow the biasing means 454 to increment the escapement wheel 452 in response to the first action of the conversion mechanism. Specifically, the anchor 456 comprises a first anchoring prong 457 and a second anchoring prong 459, and the first anchoring prong 457 and the second anchoring prong 459 interact with teeth of the escapement wheel 452 to allow the biasing means 454 to increment the escapement wheel 452 in response to the first action of the conversion mechanism.

The conversion mechanism comprises an actuator 458 in the form of a flexible membrane. In use, an inhalation on the inhaler article 200 results in a temporary increase in fluid flow rate through the fluid flow passage 322, as explained above. The temporary increase in fluid flow rate may comprise a first portion in which the fluid flow rate increases, and a subsequent second portion in which the fluid flow rate decreases, also as explained above.

As the user inhales on the inhaler article 200, a fluid flow, specifically an air flow, is drawn in through the fluid flow inlet 318 of the holder 300. This fluid flow accelerates as it passes through the venturi tube and results in a reduction in pressure in the venturi tube. This reduction in pressure acts to initiate the first action of the conversion mechanism.

The first action comprises movement of the actuator 458. Specifically, the first action comprises a departing movement of the actuator 458 from a first position to a second position, and a returning movement of the actuator 458 from the second position to the first position. The resilience of the flexible membrane naturally resists the departing movement of the actuator 458.

In the inhalation counter 450 of FIG. 3, the departing movement of the actuator 458 comprises downward movement of the actuator 458 to reach the position shown in FIG. 3. Thus, as a user begins to inhale on the inhaler article, the actuator 458 moves downwards. That is, in response to the reduction in pressure in the venturi tube, the flexible membrane flexes such that a central portion of the membrane moves downwards. This moves the anchor 456 in the same way the anchor 356 of FIG. 2 is moved by downwards movement of the piston.

Eventually, the fluid flow rate through the fluid flow passage 322 will begin to decrease. This is the second portion of the temporary increase in fluid flow rate. During, or very shortly after, this second portion of the temporary increase in fluid flow rate, the flow rate through the venturi tube will decrease and the pressure in the venturi tube will increase towards atmospheric pressure. As the pressure increases, the natural resilience of flexible membrane, or actuator 458, acts to move the actuator 458 upwards. That is, in a returning movement of the actuator 458, the actuator 458 returns from its second position back to its first position. As this happens, the anchor 456 rotates anti-clockwise about its pivot point 462 as described similarly in relation to upwards movement of the actuator 358 of FIG. 2. Thus, following the first action of the conversion mechanism, the escapement wheel 452 has undergone a single increment under the action of the biasing means 454.

The inhalation counter 450 further comprises an indication means 464 for indicating to a user information relating to an inhalation count of the inhalation counter 450. The indication means 464 comprises a pointer 466 and a substantially straight, linear scale 468. The scale 468 is numbered from 0 to 25. In this embodiment, the scale 468 remains fixed relative to the housing 302 of the holder 300. The pointer 466 points towards one of the numbers on the scale 468. For this embodiment, a substantially rectangular viewing window may be located on the holder 300 over the scale 468 and pointer 466 so that a user can see the number towards which the pointer 466 is pointing at any given time. The pointer 466 of the indication means 464 is coupled to the escapement wheel 452 so as to translate linearly upwards relative to the scale 468 when the escapement wheel 452 rotates. In this embodiment, a rack and pinion mechanism is used. Specifically, the pointer 466 is fixed to a linear gear 455, or rack, the escapement wheel 454 is coupled to an escapement wheel gear 472, or pinion, via a freewheel clutch 470, and the escapement wheel gear 472 is coupled to the linear gear 455, or rack. Thus, an incremental rotation of the escapement wheel 452 in response to an inhalation leads to a corresponding incremental rotation of the escapement wheel gear 472, and a corresponding incremental translation of the pointer 466 relative to the scale 468. In the embodiment shown in FIG. 3, this incremental translation of the pointer 466 causes the pointer 466 to point at a subsequent number on the scale 468. Thus, in the embodiment shown in FIG. 3, each inhalation results in the number pointed at by the pointer 466 increasing by one. So, if the number is set to zero before a first inhalation on the inhaler article 200, the inhalation counter 450 counts the number of inhalations on the inhaler article 200 and indicates this inhalation count to the user. However, as will be clear to one skilled in the art, the indication means 464 could indicate to the user other information relating to the inhalation count. For example, the inhalation counter 450 could count down rather than count up. The indication means 464 could also indicate to the user other information relating to the inhalation count in other ways. For example, the pointer 466 could include a coloured surface extending downwards which is approximately the length of the viewing window. Then, in response to inhalations, this coloured surface would upwards so as to slowly fill the viewing window. Filling the viewing window could indicate that the inhaler article 200 has likely been fully consumed.

The inhalation counter 450 also comprises a combined modifying and energising mechanism (not shown). The combined modifying and energising mechanism is operated by inserting the inhaler article 200 into the sleeve cavity. The mechanism is not shown in the Figures, but several options for this mechanism would be apparent to one skilled in the art. A single example is explained below.

The sleeve 306 may include a longitudinal slit extending from a top of the sleeve 306 downwards along a sidewall of the sleeve 306. A sleeve gear of a sequence of gears may be coupled to an escapement wheel gear 472 to which the escapement wheel 452 is coupled by a freewheel clutch 470. For example, when using a rack and pinion arrangement as shown in the embodiment of FIG. 3, the sleeve gear may be coupled, via the sequence of gears, to the rack to which the escapement wheel gear 472 is coupled. This sleeve gear may also extend partially through the slot and into the sleeve cavity. When a user inserts the inhaler article 200 into the sleeve cavity 308, the inhaler article 200 may engage with the sleeve gear and cause the sleeve gear to rotate as the inhaler article 200 is inserted deeper into the sleeve cavity 308. The sequence of gears couple this sleeve gear to the escapement wheel gear 472 so that, as the sleeve gear rotates, the escapement wheel gear 472 also rotates. Specifically, as the sleeve gear rotates, the escapement wheel gear 472 rotates in an anti-clockwise direction, thereby moving the pointer 466 downwards and compressing the helical spring, or biasing means 454. However, since the escapement wheel gear 472 is coupled to the escapement wheel 452 by the freewheel clutch 470, anti-clockwise rotation of the escapement wheel gear 472 does not rotate the escapement wheel 452. In this manner, engaging the inhaler article 200 with the holder 300, specifically inserting the inhaler article 200 into the sleeve cavity, operates the combined modifying and energising mechanism to reset the pointer 466 to zero and energise the biasing means 454. The sleeve gear may similarly be coupled to the sequence of gears by a freewheel clutch. This would ensure that any rotation of the sleeve gear in an opposite direction as the inhaler article 200 is removed from the sleeve cavity 308 does not act to cause rotation of the escapement wheel gear 472.

Figure 4:
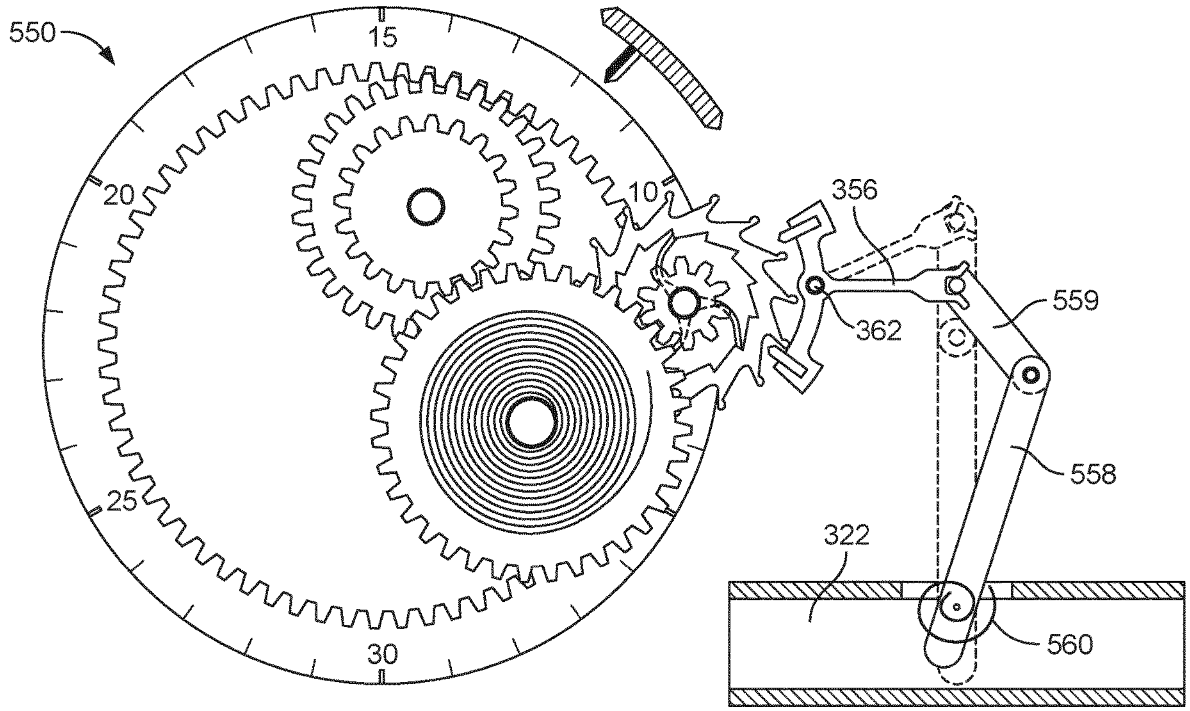
FIG. 4 is a cross-sectional view of a second alternative inhalation counter for an inhalation system.

FIG. 4 is a cross-sectional view of a second alternative inhalation counter 550 for an inhalation system. For example, the inhalation counter 550 could replace the inhalation counter 350 used in the inhalation system of FIG. 1.

The inhalation counter 550 is identical to the inhalation counter 350 shown in FIG. 2 except that the actuator 358 in the form of a piston has been replaced by an actuator 558 in the form of a rotatable flap, the resistance component 360 in the form of a helical spring has been replaced by a resistance component 560 in the form of a torsional spring, and the actuator 558 is now coupled to the anchor 356 via a connecting rod 559. In the embodiment shown in FIG. 4, the first action of the conversion mechanism comprises rotation of the actuator 558 in a first direction, followed by rotation of the actuator in a second direction opposite to the first direction. This is explained in more detail below. Otherwise, the inhalation counter 550 of FIG. 4 functions in the same way as the inhalation counter of FIG. 2.

The inhalation counter 550 of FIG. 4 comprises an actuator 558 in the form of a rotatable flap. At least a portion of the flap is located in the fluid flow passage 322. The flap is urged towards a forward position, shown as a dotted line in FIG. 4, by the resistance component 560. The inhalation counter 550 comprises a connecting rod 559. A first end of the connecting rod 559 is pivotably connected to the anchor 356, and a second end of the connecting rod 559 pivotably connected to the flap.

In use, a user inhaling on the inhaler article 200 results in an air flow through the air flow passage 322 impinging upon the flap. During a first portion of the air flow, the air flow exerts a force on the flap acting to rotate the flap towards a back position, shown as a solid line in FIG. 4. This rotation from the forward position to the back position may be termed the departing movement of the actuator 558 and corresponds to downwards movement of the piston in FIG. 2. This motion causes the connecting rod 559 to move, thereby rotating the anchor 356 about its pivot point 362. Thus, rotation of the flap from the forward position to the back position causes rotation of the anchor 356 in the same way as downwards movement of the piston of the inhalation counter 350 of FIG. 2.

Towards the end of the inhalation, the air flow rate through the air flow passage 322 reduces. Thus, under the action of the resistance component 560 in the form of a torsional spring, the flap rotates from the back position to the forward position. This may be termed the returning movement of the actuator 558 and corresponds to upwards movement of the piston in FIG. 2. This motion causes the connecting rod 559 to move, thereby rotating the anchor 356 about its pivot point 362. Thus, rotation of the flap from the back position to the forward position causes rotation of the anchor 356 in the same way as upwards movement of the piston of the inhalation counter 350 of FIG. 2. This completes the first action of the conversion mechanism. All other details of the inhalation counter 550 of FIG. 4 are identical to the inhalation counter 350 of FIG. 2.

For the purpose of the present description and of the appended claims, except where otherwise indicated, all numbers expressing amounts, quantities, percentages, and so forth, are to be understood as being modified in all instances by the term “about”. Also, all ranges include the maximum and minimum points disclosed and include any intermediate ranges therein, which may or may not be specifically enumerated herein. In this context, therefore, a number A is understood as A ±10% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhalation counter for an inhalation system, the inhalation system comprising a fluid flow passage and the inhalation counter comprising:

an escapement wheel;

a biasing means for incrementing the escapement wheel;

a conversion mechanism which, in use, is configured to perform a first action in response to a temporary increase in fluid flow rate through the fluid flow passage; and an anchor, wherein the anchor is coupled to the conversion mechanism and configured to interact with the escapement wheel so as to allow the biasing means to increment the escapement wheel during or at and end of the first action of the conversion mechanism.

2. An inhalation counter according to claim 1, wherein the temporary increase in fluid flow rate comprises a first portion in which the fluid flow rate increases, and a subsequent second portion in which the fluid flow rate decreases, and wherein the conversion mechanism is configured to initiate the first action in response to the first portion of the temporary increase in fluid flow rate and complete the first action in response to the second portion of the temporary increase in fluid flow rate.

3. An inhalation counter according to claim 1, wherein the conversion mechanism comprises an actuator and the first action comprises movement of the actuator.

4. An inhalation counter according to claim 3, wherein the first action comprises a departing movement of the actuator from a first position to a second position, and a returning movement of the actuator from the second position to the first position, and the conversion mechanism comprises a resistance component configured to resist the departing movement of the actuator.

5. An inhalation counter according to claim 1, wherein the conversion mechanism comprises a rotatable component and the first action comprises rotation of the rotatable component.

6. An inhalation counter according to claim 1, wherein the conversion mechanism comprises a flexible component and the first action comprises flexing of the flexible component.

7. An inhalation counter according to claim 1, wherein the inhalation counter comprises an indication means for indicating to a user information relating to an inhalation count of the inhalation counter.

8. An inhalation counter according to claim 7, wherein the inhalation counter comprises a modifying mechanism coupled to the indication means for modifying the information relating to the inhalation count.

9. An inhalation counter according to claim 8, wherein the modifying mechanism is configured to allow the user to set the information relating to the inhalation count.

10. An inhalation counter according to claim 7, comprising a combined modifying and energising mechanism for modifying the information relating to the inhalation count and energising the biasing means.

11. An inhalation counter according to claim 10, wherein the combined modifying and energising mechanism comprises a freewheel clutch.

12. An inhalation counter according to claim 1, comprising an energising mechanism for energising the biasing means.

13. A holder for use with an inhaler article, the holder comprising an inhalation counter according to claim 1.

14. A holder according to claim 13, wherein the inhalation counter comprises an indication means for indicating to a user information relating to an inhalation count of the inhalation counter, the inhalation counter comprises a modifying mechanism coupled to the indication means for modifying the information relating to the inhalation count, and the modifying mechanism is operated by one or both of engaging the inhaler article with the holder and disengaging the inhaler article from the holder.

15. A holder according to claim 13, wherein the inhalation counter comprises an energising mechanism for energising the biasing means, and the energising mechanism is operated by one or both of engaging the inhaler article with the holder and disengaging the inhaler article from the holder.

16. A holder according to claim 13, wherein the inhalation counter comprises an indication means for indicating to a user information relating to an inhalation count of the inhalation counter, the inhalation counter comprises a combined modifying and energising mechanism for modifying the information relating to the inhalation count and energising the biasing means, and the combined modifying and energising mechanism is operated by one or both of engaging the inhaler article with the holder and disengaging the inhaler article from the holder.

17. An inhalation system comprising an inhaler article and a holder according to claim 13.

* * * * *